United States Patent

Harris et al.

Patent Number: 5,112,356
Date of Patent: May 12, 1992

[54] LOWER LIMB PROSTHESIS WITH MEANS FOR RESTRICTING DORSI-FLEXION

[75] Inventors: Graham J. Harris, Basingstoke; Victor J. Woolnough, North Waltham, both of England

[73] Assignee: Chas A. Blatchford & Sons Limited, Basingstoke, England

[21] Appl. No.: 661,440

[22] Filed: Feb. 25, 1991

Related U.S. Application Data

[63] Continuation-in-part of Ser. No. 318,917, Mar. 3, 1989.

[30] Foreign Application Priority Data

| Mar. 4, 1988 | [GB] | United Kingdom | 8805191 |
| Dec. 23, 1988 | [GB] | United Kingdom | 8830149 |
| Feb. 28, 1990 | [GB] | United Kingdom | 9004430 |
| Dec. 19, 1990 | [GB] | United Kingdom | 9027531 |

[51] Int. Cl.⁵ ............................................. A61F 2/66
[52] U.S. Cl. ............................ 623/49; 623/48; 623/50; 623/52; 623/53; 623/55
[58] Field of Search ............... 623/47–49, 623/53–55, 50–52, 56

[56] References Cited

U.S. PATENT DOCUMENTS

| 2,677,825 | 5/1954 | Richardson et al. | 2/61 |
| 3,784,988 | 1/1974 | Trumpler. | |
| 4,461,045 | 7/1984 | Shorter et al. | 623/47 X |
| 4,645,509 | 2/1987 | Poggi et al. | 623/55 |
| 4,652,266 | 3/1987 | Truesdell | 623/55 |
| 4,892,553 | 1/1990 | Prahl | 623/55 |

FOREIGN PATENT DOCUMENTS

| 0550954 | 5/1932 | Fed. Rep. of Germany | 623/53 |
| 3430207 | 2/1986 | Fed. Rep. of Germany | 623/49 |
| 0800547 | 1/1936 | France | 623/55 |
| 2138082 | 12/1972 | France. | |
| WO85/04095 | 9/1985 | PCT Int'l Appl. . | |
| 92523 | 1/1921 | Switzerland. | |
| 105293 | 4/1917 | United Kingdom. | |
| 120445 | 11/1918 | United Kingdom. | |
| 0738845 | 10/1955 | United Kingdom | 623/55 |
| 2070439 | 9/1981 | United Kingdom. | |
| 2092451 | 8/1982 | United Kingdom | 623/47 |
| 2161390 | 1/1986 | United Kingdom | 623/48 |
| 2202448 | 9/1988 | United Kingdom. | |
| 2216423 | 11/1989 | United Kingdom. | |
| 8400681 | 3/1984 | World Int. Prop. O. | 623/54 |

Primary Examiner—Randall L. Green
Assistant Examiner—D. Willse
Attorney, Agent, or Firm—Hale and Dorr

[57] ABSTRACT

In a lower limb prosthesis an energy storing foot is combined with a resilient ankle joint which is arranged to allow planatar flexion but substantially to prevent dorsiflexion. The ankle joint comprises a ball and socket joint, the socket of which is extended downwardly on the anterior, medial and lateral sides to for a skirt positioned so as to compress a resilient ring encircling a ball member of the ball and socket joint. Metal plates are embedded in the anterior part of the ring to prevent significant dorsiflexion. The foot has a keel having a lower spring portion connected at its posterior end as a cantilever to an upper ankle mounting portion. These two portions may be formed as a single carbon fibre reinforced plastics moulding or individually as part of a two-piece keel with the ankle mounting portion rigid and the spring portion as simple fibre-reinforced strip. The resilience of the foot is adjustable by means of a displaceable resilient buffer element mounted ahead of the ankle centre as a coarse adjustment device and/or by means of a transversely extending support bar which can be moved longitudinally behind the ankle centre by rotating an adjusting screw. The screw passes through an aperture in the keel and is accessible at the rear of the heel.

9 Claims, 4 Drawing Sheets

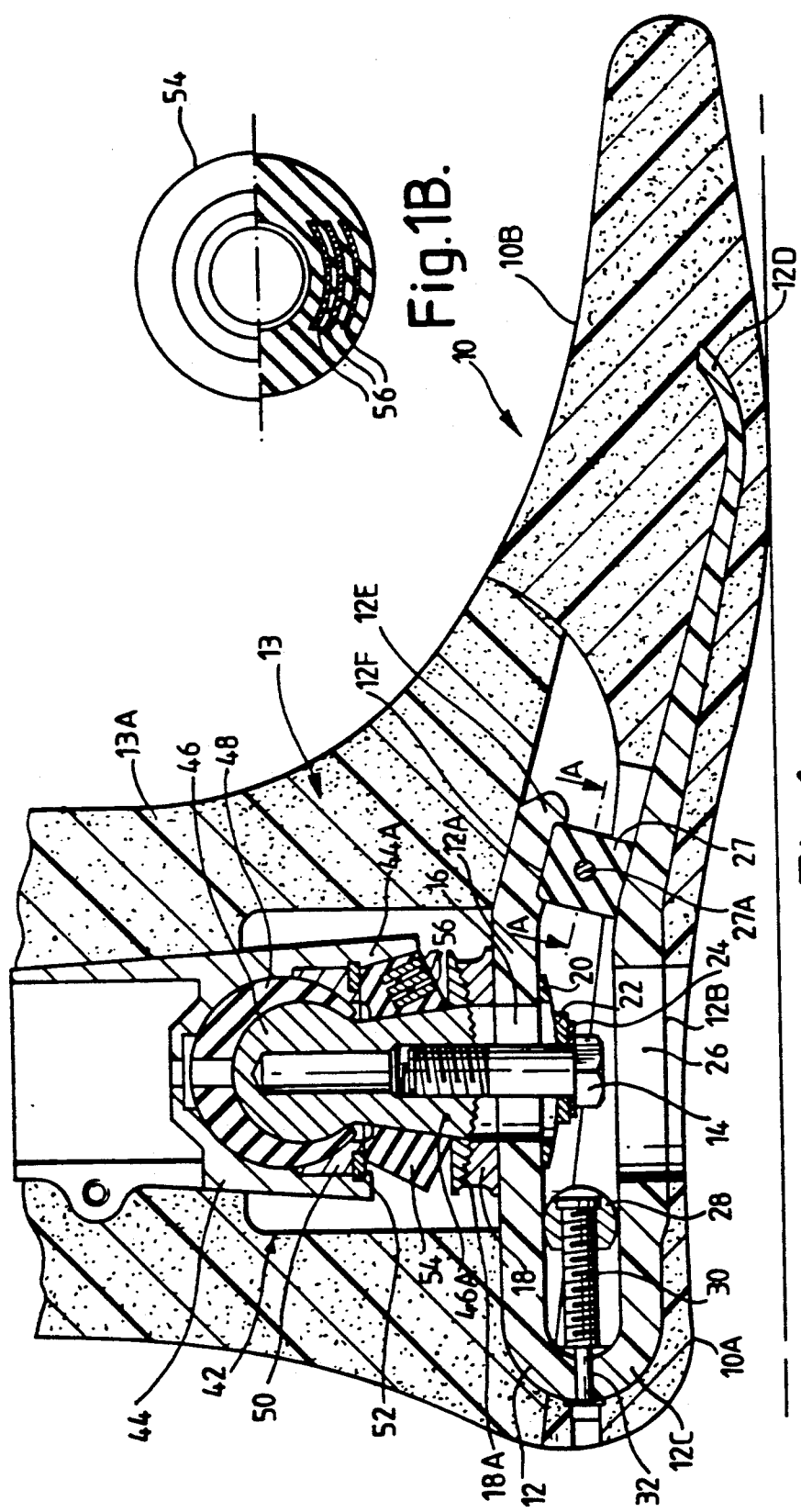

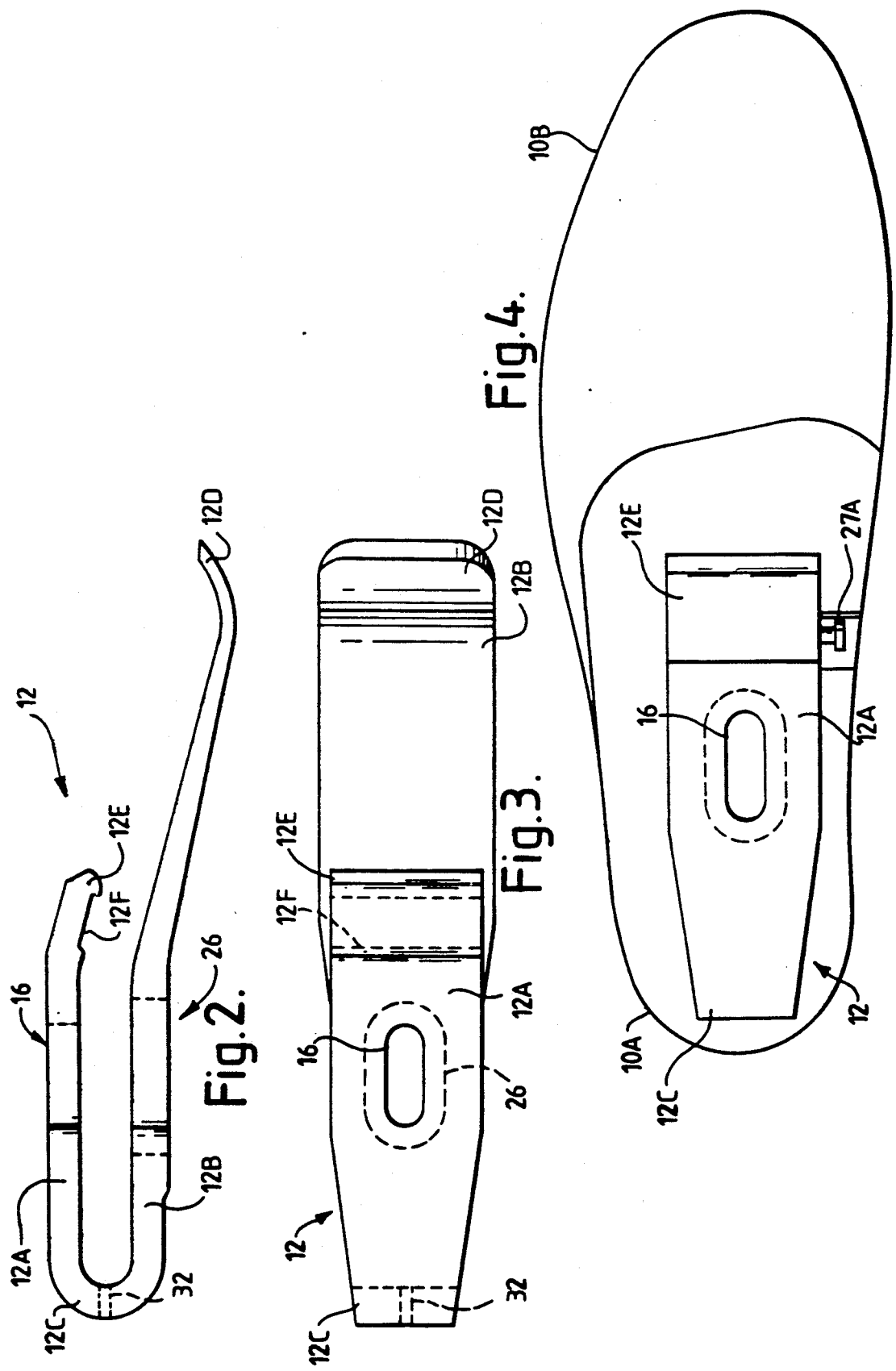

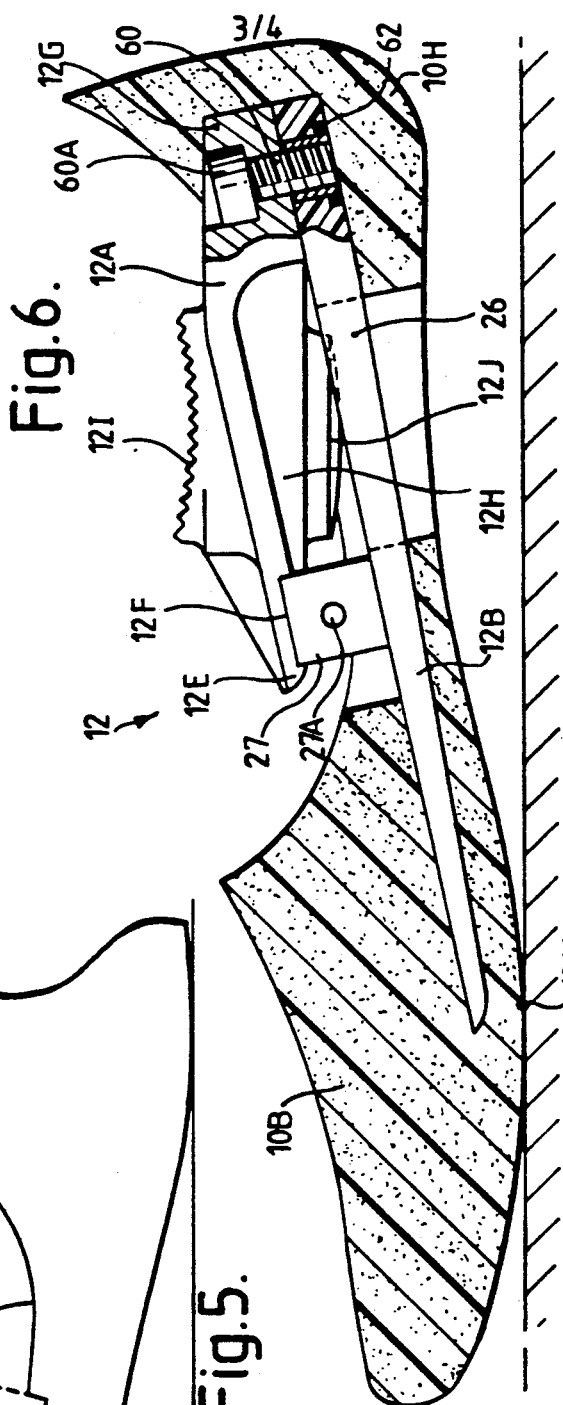
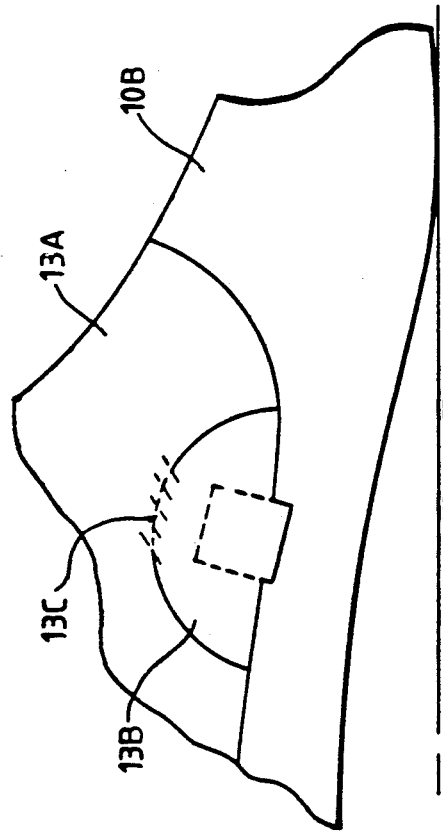
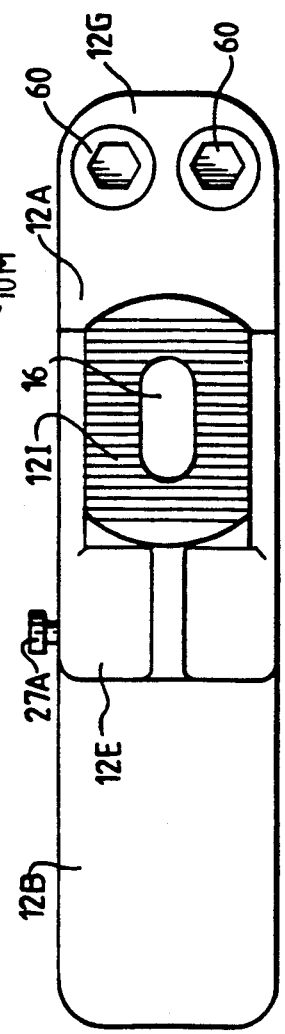

LOWER LIMB PROSTHESIS WITH MEANS FOR RESTRICTING DORSI-FLEXION

CROSS REFERENCE TO RELATED APPLICATION

This Application is a Continuation-in-Part of application Ser. No. 318,917 filed Mar. 3rd, 1989.

BACKGROUND OF THE INVENTION

This invention relates to a lower limb prosthesis and to an artificial foot.

It is well known that an artificial foot can be provided with an energy storing resilient element to assist an amputee in obtaining a natural and comfortable gait and, in the case of the relatively active amputee, in running. In one known arrangement, the resilient element comprises a resilient elongate keel in the form of a cantilever portion extending forwardly from an integral upper connecting member having an interface for connection to an ankle or shin member. To achieve a required degree of dorsi-flexion under load the cantilever portion is joined by an integral resilient heel portion to the upper member at a position adjacent the heel of the foot. As the patient transfers weight following heel contact, the keel flexes, storing potential energy which is then converted into kinetic energy on "push-off". Such feet have limitations for walking.

SUMMARY OF THE INVENTION

It is an object of this invention to provide a prosthesis in which the benefit of an energy storing foot, i.e. its ability to propel the patient at "push-off", is obtained under a variety of conditions.

It is a further object of the invention to provide a prosthesis in which the stiffness of the foot can be varied to suit different conditions and different patients.

Yet a further object of the invention is the provision of a prosthesis including an energy storing foot which is simple and inexpensive to manufacture.

The invention includes a lower limb prothesis which comprises an energy storing foot having an anterior portion and an ankle mounting portion, and is resiliently deformable such that the anterior portion is able to execute an energy-storing dorsi movement relative to the ankle mounting portion. Coupled to the foot is an ankle joint assembly having a first part for connection to an upper component of the prosthesis, a second part attached to the ankle mounting portion of the foot at a foot-mounting interface, and means connecting the second part to the first part allowing plantar flexion of the ankle joint assembly relative to a neutral state but substantially preventing dorsi-flexion. The position of the foot relative t the second part of the ankle joint assembly is adjustable at the foot mounting interface.

By combining a flexible ankle joint with an energy storing foot in this manner, the walking characteristics associated with prior limbs with energy-storing feet are much improved upon, the limitation of dorsi-flexion in the ankle joint allowing use of the energy-storing property of the foot for aiding "push-off" during the walking or running cycle.

The maximum angle of dorsi-flexion is considerably less than the maximum angle of plantar flexion, and is preferably less than 3°. Of the total dorsi-flexion of the assembly of the foot and the ankle joint, the contribution due to the ankle joint over the majority of the range of the total dorsi-flexion is normally less than 30 per cent. In contrast, of the total plantar flexion of the combination of the foot and the ankle joint, over the majority of the total plantar flexion range, the plantar flexion contribution due the ankle joint preferably exceeds 85 per cent of the total. Generally, the rate of resistance of the joint to dorsi-flexion is at least ten times that for plantar flexion in terms of angular deflection per unit moment applied.

Improved walking characteristics can be obtained if the ankle joint is able to execute not only planar flexion, but also medial and lateral flexion. Such flexion properties may be obtained by constructing the ankle joint assembly as a ball and socket joint, the connection means between the first and second parts of the assembly including a resilient ring around the shank of the ball member of the ball and socket joint, and by arranging for the socket portion of the joint to extend around the shank outside the ring in the form of a skirt. When the ankle joint is flexed, the ring is compressed between the skirt and the ball member shank to resist flexion. The skirt may be arranged so as to engage the ring only by the resistance of the ball and socket joint itself, while medial, lateral and dorsi-flexion are additionally resisted by the ring. For virtual prevention of dorsi-flexion of the ankle joint, the ring may have one or more stiffening elements embedded in its anterior portion.

The invention also includes a lower limb prosthesis comprising: an energy-storing foot comprising a keel which has an anterior portion and an ankle mounting portion, and is resiliently deformable such that the anterior portion is able to execute an energy-storing dorsi movement relative to the ankle mounting portion, the anterior portion forming part of a lower keel portion extending lengthwise in the foot from a heel part of the foot to an anterior part of the foot, the keel further comprising a posterior connecting portion connecting the ankle mounting portion of the keel to the lower keel portion in the heel part of the foot; and an ankle joint assembly having a first part for connection to an upper component of the prosthesis, a second part connected to the ankle mounting portion of the keel, and means connecting the second part to the first part and arranged to allow plantar flexion of the ankle joint assembly from a neutral state but substantially to prevent dorsi-flexion; the foot further comprising a dorsi-flexion restricting device for location between an anterior end part of the ankle mounting portion of the keel and the lower keel portion.

A particularly simple and effective keel construction which may be adopted is a resilient single-piece fibre-reinforced plastics strip U-shaped in side elevation, with the lower keel portion extending from the heel portion of the foot into the region of the ball of the foot.

Restricting the dorsi-flexion of the keel in this way provides extra stiffness for active patients, especially for running. The further in front of the shin axis or ankle joint centre the restricting device is placed, the greater is its effect in reducing dorsi-flexion of the keel. In one preferred embodiment of the invention, the restricting device is a removable block of elastomeric material mounted between an anterior extension of the ankle mounting portion of the keel and the lower keel portion. Preferably, also, further means for adjusting the resistance of the keel to dorsi-flexion are provided in the form of a longitudinally adjustable support member located behind the shin axis or ankle centre and coupling a posterior part of the ankle mounting portion of the keel to the lower keel portion. Typically, the support member comprises a bar extending transversely of the foot between the ankle mounting portion of the keel and the lower keel portion, the bar being adjustably located by a longitudinally acting screw passing through an aperture in the said posterior connecting portion of the keel to be accessible at the rear of the foot. Such an assembly permits a wide range of keel stiffnesses to be obtained without altering the keel structure itself. Thus, the overall stiffness of the keel is affected both by the position of the longitudinally adjustable support member (as a fine adjustment) and the absence or presence of one of a series of elastomeric blocks of different hardnesses (as a coarse adjustment), thereby accommodating a wide range of patient weights and activity levels.

In another of its aspects, the invention includes an energy storing artificial foot comprising: a keel having an upper load receiving portion, an elongate resiliently deflectable lower portion extending lengthwise in the foot from a heel portion of the foot to an anterior portion of the foot, the load receiving portion being connected to the lower keel portion in the heel portion of the foot; and a dorsi-flexion restricting device for location between an anterior end part of the load receiving portion and the lower keel portion.

The invention provides a lower limb prosthesis and an artificial foot in which the resilience of the energy storing keel is not only adjustable by means of an adjusting control, but can also be temporarily altered without losing the setting produced by operating the adjusting control. Thus, for example, a keel stiffness for walking can be set by means of a screw adjuster, while a higher stiffness for running may be obtained if required by adding a removable dorsi-flexion restricting element which does not affect the screw adjuster.

In another keel construction in accordance with the invention, the keel comprises a resilient lower keel portion extending from a heel region of the foot at least into a metatarsal region of the foot, and a separately formed upper keel portion secured to the lower keel portion in the heel region and extending forwardly from the heel region to form a mounting part for mounting an upper limb component, the mounting part being spaced from the lower keel portion. The lower keel portion is preferably of plastics material, particularly a fibre-reinforced plastics material, and being formed separately from the upper keel portion, can be a component that is relatively easy to mould. For example, the lower keel portion may be formed as a single elongate strip or plate, preferably tapered in thickness from the heel region forwardly. The upper keel portion may be a substantially rigid component formed from, for example, fibre reinforced plastics or a metallic material such as aluminum alloy. The upper keel portion extends in an anterior-posterior direction, and may be generally in the form of a plate having a depending thickened posterior end part for housing a connecting element or elements securing the upper keel portion to the lower keel portion in the heel region of the foot. In this way, much of the resilience of the above-mentioned single U-shaped fibre-reinforced plastics keel is retained with a component which is simpler, and hence cheaper, to mould. This embodiment also offers the possibility of economical production of a range of keels of different stiffnesses for a given foot size. In its preferred form of a substantially rigid block, the upper keel portion allows a relatively high foot attachment bolt torque to be applied without damage to the keel, which is of advantage for active and heavy patients.

While the mounting part of the upper keel portion may be integral with the upper limb component (e.g. a shin component or part of a shin component) or ankle joint, the preferred embodiment of the invention has this mounting part provided with an interface for detachable mounting of the foot. This interface may be shaped to allow different heel height settings to be obtained. Typically, the mounting part mounts the upper limb component by having an oval aperture passing through the interface for housing a bolt threaded into the upper limb component.

The element for connecting the upper keel portion to the lower keel portion is preferably at least one bolt or rivet passing through the depending posterior end of the upper keel portion. In the case of a bolt, a threaded insert may be provided in the posterior end part of the lower keel portion.

A resilient buffer element may be fitted between an anterior end nose of the upper keel portion and the lower keel portion to modify the stiffness of the keel. A recess is provided in the lower face of the upper keel portion for locating this buffer element.

The foot may be connected to an ankle joint or directly to a shin member forming part of the prothesis and may be detachable from or integral with parts of the ankle joint and/or shin member.

The invention is described in more detail below by way of example with reference to the drawings.

BRIEF DESCRIPTION OF THE DRAWINGS

FIG. 1 is a vertical cross-section of a lower limb prosthesis in accordance with the invention, viewed from one side.

FIG. 1A is a cross-section of a buffer element taken on a plane extending transversely of the prosthesis as shown by the line A—A in FIG. 1.

FIG. 1B is a partly sectioned plan view of a snubber ring forming part of an ankle joint of the prosthesis of FIG. 1.

FIG. 2 is a side elevation of a keel for a foot forming part of the prosthesis of FIG. 1.

FIG. 3 is a plan view of the keel.

FIG. 4 is a plan view of the foot shown in FIG. 1.

FIG. 5 is a side elevation of part of the prosthesis of FIG. 1.

FIG. 6 is a partly sectioned side elevation of a alternative artificial foot.

FIG. 7 is a plan view of a keel of the foot of FIG. 6.

DESCRIPTION OF THE PREFERRED EMBODIMENTS

Figure 8:
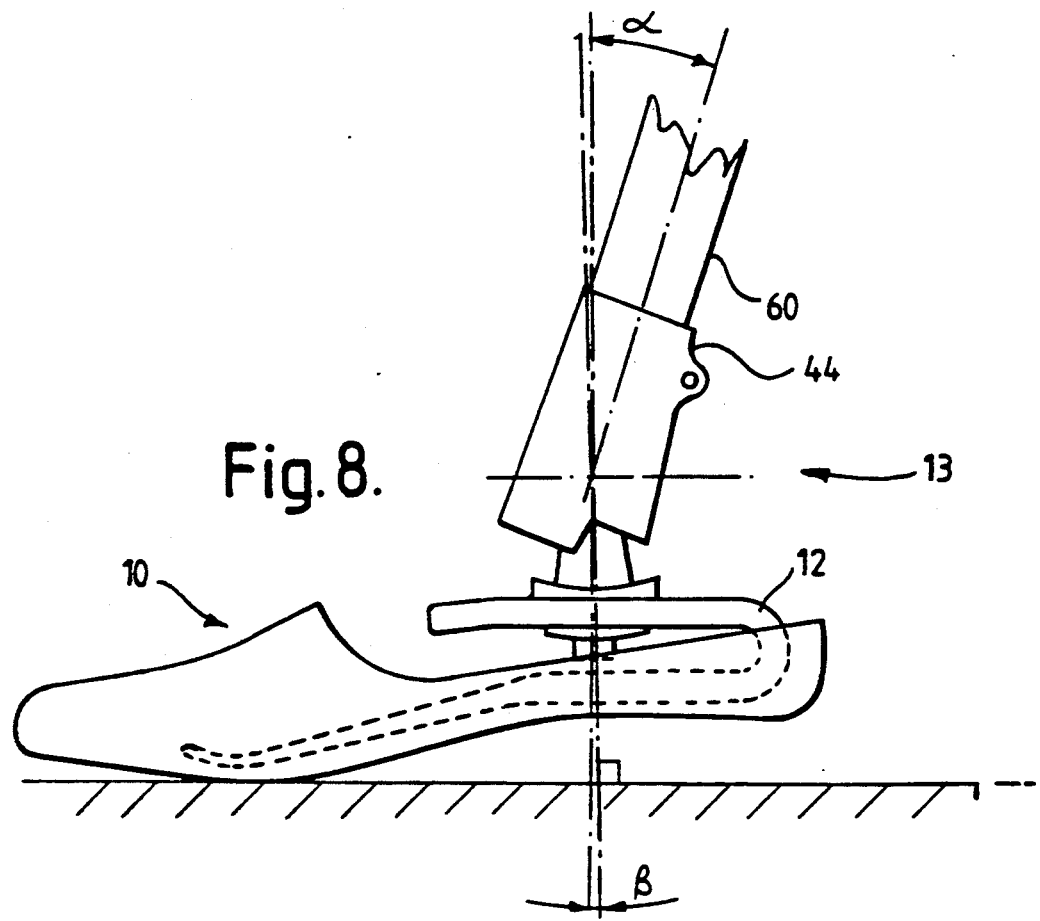
FIG. 8 is a diagrammatic side elevation of a prosthesis in accordance with the invention, shown in a plantar-flexed condition.

Referring to FIGS. 1 to 4, a first lower limb prosthesis in accordance with the invention includes a foot 10 with an endoskeletal structure comprising a single-piece carbon-fibre reinforced plastics keel 12 having an upper plate portion 12A for mounting an ankle joint 13 for receiving loads through the ankle joint, and an integral elongate lower portion 12B in the form of a strip running lengthwise of the foot for transmitting the loads to the sole of the foot. The upper and lower keel portions 12A and 12B are joined together at their posterior ends adjacent the heel 10A of the foot by an integral curved connecting portion 12C so that the three portions 12A, 12B and 12C of the keel constitute a U-shaped section in side elevation, in the form of a folded strip.

The lower keel portion 12B is parallel-sided in its anterior region and terminates in the region of the ball of the foot in an upwardly directed lip 12D. Its thickness increases in the posterior direction, while the width narrows to a minimum in the connecting portion 12C. The upper plate portion 12A is also parallel-sided in its anterior region which terminates in an anterior end part 12E and is generally wider than the connecting portion. The lower keel portion 12B is seated in a moulded flexible polyurethane foam cosmesis 10B corresponding approximately in shape to the shape of the natural foot, while the ankle 13 is enclosed by the lower part of a shin cosmesis 13A. The two cosmesis parts 10B and 13A abut each other at a level below that of the upper plate portion 12A of the keel.

Attachment of the upper keel portion 12A to the ankle joint 13 is achieved by means of a vertical bolt 14 which passes through an oval aperture 16 in the upper portion 12A and is threaded in the joint 13 (FIG. 1). Washers 18 and 20 are placed above and below the upper keel portion 12A to allow adjustment of the foot angle (in effect a heel height adjustment), the upper washer 18 having a serrated concave cylindrical surface 18A for mating with a corresponding convex surface on the ankle joint 13, and the lower washer 20 having a coaxial convex lower surface to allow proper seating of the head of the bolt 14 across the range of adjustment. Packing washers 22 and 24 are provided between the head of the bolt 14 and the convex washer 20. Access to the bolt head is gained via a second oval aperture 26 in the lower keel portion 12B and in the cosmesis 10B.

The stiffness of the keel 12 may be altered by inserting or removing, as required, a buffer element in the form of an elastomeric block 27 between the anterior end part 12E of the upper keel portion 12A and the lower keel portion 12D directly beneath.

A recess 12F is provided on the underside of the upper keel portion anterior end part 12E to house the buffer 27 when in place, and the buffer 27 itself has a transverse pin 27A which protrudes on the medial side of the foot as shown in FIG. 1A to aid insertion and removal.

Referring to FIG. 5, access to the buffer pin 27A is gained by lifting a hinged flap 13B of the shin cosmesis 13A, the flap being a displaceable cover hinged along its upper edge 13C as shown and extending to the lower edge of the shin cosmesis 13A where it meets the foot cosmesis 10B in order to cover an aperture in the cosmesis in registry with the buffer 27.

The degree to which the keel stiffness is increased by inserting the buffer element 27 depends on the hardness of the elastomeric material making up the block. It will be appreciated, then, that the keel stiffness can be varied in steps by providing blocks of different hardnesses.

Further variation in the stiffness of the keel 12, particularly when the buffer element 27 has been removed or is made of a very soft material, is achieved by means of a support member 28 which couples the upper portion 12A to the lower portion 12B by engaging the lower and upper surfaces respectively of these members between the posterior connecting portion 12C and the bolt 14. The support member 28 comprises a transversely arranged aluminum alloy bar having a threaded central hole bored across it to receive a longitudinally positioned adjusting screw 30. The screw 30 passes through a bore 32 (see FIG. 2) cut in the connecting portion 12C of the keel to emerge on the posterior face of the keel where it has a head 36 having a hexagon socket to suit an Allen key. The screw 30 is accessible at the heel of the foot where it can be rotated by a prosthetist or the patient.

It will be appreciated that the combination of the buffer element 27 and the adjustable support member 28 allows the stiffness of the keel to be adjusted over a wide range to suit the weight of the patient and his or her level of activity, thereby reducing the range of keels that need to be provided to suit patients of different sizes, weights, and activities. It is even possible for patients themselves to alter the keel stiffness temporarily to suit a particular activity.

To achieve good walking characteristics, the artificial foot 10 described above is combined with an ankle joint 13 allowing plantar ankle flexion and medial/lateral flexion but substantially preventing dorsi-flexion. Such a combination allows the benefits of ankle flexion to be retained together with the ability to store energy in the keel of the foot during the period immediately prior to "push-off" in the walking or running cycle.

Referring to FIGS. 1 and 1B, an example of an ankle joint 13 having the required flexion characteristics is in the form of a ball and socket joint 42. The joint 42 has a socket member formed by an upper limb component which, in this example, is the lower end portion 44 of a shin member. The socket member 44 houses a ball member 46 bolted to the upper portion 12A of the keel 12. A resilient part-spherical cover 48 is fitted over the ball member 46, the assembly of the ball member 46 and the cover 48 being clamped in the socket member 44 by an internal ring 50 held in position by an expanding circlip 52 housed in a groove in the shin member end portion 44.

The shin member end portion 44 has a depending skirt 44A extending around and spaced from a connection shank part 46A of the ball member 46. Between the skirt 44A and the shank 46A is a resilient snubber ring 54. The skirt 44A overlies only the medial, anterior and lateral outer faces of the snubber ring 54 thereby restricting medial, dorsi- and lateral flexion of the ankle joint, the plantar flexion allowed by the ball and socket joint being largely unaffected. To further restrict dorsi-flexion, the snubber ring 54 has encapsulated within its anterior portion a plurality of stiffening plates 56 which serve to restrict the resilience of the snubber ring in its anterior portion so as to increase further the resistance of the ankle joint to dorsi-flexion. Each plate 56 comprises an elongate rigid metal strip curved about an axis parallel to its surfaces and its end, and each is positioned transversely in the snubber ring 54 with its surfaces generally parallel to the outer part-conical surface of the ring 54. Restriction of dorsi-flexion is brought about not so much as a result of the presence of less rubber material in the anterior portion of the ring than in the medial or lateral portions, but rather by virtue of the limitation of the upward, downward and transverse deformation of the rubber material caused by the plates and their adhesion to the rubber material.

The ankle joint described above is a development of a joint disclosed in British Patent Specification No. 2161390A, the content of which is incorporated in this specification by reference.

Other means of restricting dorsi-flexion of the ankle joint may be employed. For instance, the plates 56 may be replaced by a single block of rigid material embedded in and/or bonded to the snubber ring.

Referring now to FIGS. 6 and 7 of the drawings, an alternative keel construction may be used in accordance with the invention. In this alternative construction, the keel 12 comprises a resilient lower keel portion 12B in the form an elongate plate moulded from carbon-fibre-reinforced plastics material. This plate 12B extends in an anterior-posterior direction in the foot from the heel region 10H of the foot to the metatarsal region 10M, tapering in thickness in the anterior direction with a more pronounced taper at the extreme anterior end.

Attached to the posterior end of the lower keel portion is an upper keel portion 12A which, in this embodiment, is a machined aluminum alloy plate which extends generally parallel to the lower keel portion 12B in the anterior-posterior direction, and which has a depending posterior end part 12G which abuts an upper surface of the posterior end part of the lower keel portion 12B. Two bolts 60 having their bolt heads 60A housed in the posterior end portion 12G of the upper keel portion 12A pass through bores in the posterior end part 12G and are threaded in inserts 62 embedded in the posterior end part of the lower keel portion 12B. It will be appreciated that other means for clamping the upper keel portion to the lower keel portion may be used, such as a clamping sleeve around the posterior end parts of both portions, or rivets in place of the bolts 60.

To add to the rigidity of the upper keel portion, one or more webs 12H are formed between the lower surface of the plate and the depending posterior end portion.

In order that the foot may be adjustably mounted on an upper limb component such as the ball and socket joint shown in FIG. 1 the interface with the ankle joint, as before, comprises a raised mounting projection having a serrated concave cylindrical surface 12I. In the present embodiment, a boss 12J extends downwardly from the plate of the upper keel portion 12A in registry with the mounting interface 12I, the lower surface of the boss 12J being generally cylindrical and convex to receive the head of a bolt (not shown) passing through an oval slot 16 passing through the upper keel portion 12A for fixing the upper keel portion 12A to the ankle joint. A slot 26 is provided in the lower keel portion to allow access to the bolt fixing the ankle joint and to provide a clearance for part of the boss 12J.

As in the embodiment of FIG. 1, a rubber buffer 27 of selected hardness is fitted between an anterior nose 12E of the upper keel portion and the upper surface of the lower keel portion 12B, the buffer being removable so that the resilience of the keel can be modified according to the patient's requirements between a "soft" setting, in which the buffer 27 is removed and in which the complete length of the keel provides an energy-storing function, and a "hard" setting in which the buffer 27 acts as a deformable fulcrum. Evidently, buffers of different hardnesses can be used. Location of the buffer 27 is provided by a recess 12F in the downwardly directed surface of the anterior nose 12E, and insertion and removal is accomplished by means of a pin 27A or a similar projection forming part of the buffer 27, access being gained through a flap in the foot cosmesis as in the embodiment shown in FIGS. 1 to 5.

At least the lower keel portion 12B is encased in a foam cosmesis 10B in known manner, the cosmesis being shaped to resemble the natural foot.

While the foot particularly described here and shown in FIGS. 6 and 7 is intended for mounting to a resilient ankle joint, the upper keel portion may be integral with a shin component or may be bolted directly to a shin component, in which case it is preferable to provide a heel cushion of a different material from that of the cosmesis beneath the posterior end part of the lower keel portion 12B.

To deal now with the flexion characteristics of the ankle joint shown in FIGS. 1 and 1A and in particular the effect of the stiffening plates 56 in the snubber ring 54, some initial dorsi movement of the foot will be taken up by the joint 13, but this is limited to less than 3°, and over the majority of the range of combined dorsi-flexion of the foot 10 and the joint 13, the dorsi-flexion due to flexion of the joint 13 is less than 30 per cent of the total. In contrast the joint 13 presents comparatively little resistance to plantar flexion, to the extent that the flexion of the joint 13 during the range of combined plantar flexion of the joint 13 and the foot 10 represents at least 85 per cent of the total. These properties are illustrated in FIGS. 8 and 9.

Referring to FIG. 8, when the combination of a downward force along the shin axis and a plantar moment about the ankle joint axis is applied to a shin tube 60 mounted in the upper component 44, the ankle joint 13 executes plantar flexion, as shown, by an angle $\alpha$. The keel 12 also contributes to the total plantar flexion of the arrangement, producing a further flexion of angle $\beta$. However, the rate of resilience of the ankle joint 13 is such that the angle $\alpha$ is greater than or equal to $0.85(\alpha+\beta)$. These angles can be measured by measuring the deviation of the shin tube axis from a rest position corresponding to the state of the foot and ankle joint when no external load is applied, to a flexed position when the force and moment referred to above are applied. The required combination of downward force and posterior moment may be produced for test purposes by holding the foot 10 in a nest or cradle (not shown) with the shin axis perpendicular to a ground plane (typically, the lower surface of the heel of the foot is 15 mm above the ground plane with the sole in the region of the ball of the foot touching the plane) and then applying a vertically downwardly directed load on a bracket (not shown) rigidly attached to the shin tube 60, the length and position of the bracket being such that the load acts through a point 60 mm behind the shin axis and 150 mm above the axis of rotation of the ankle joint 13.

Figure 9:
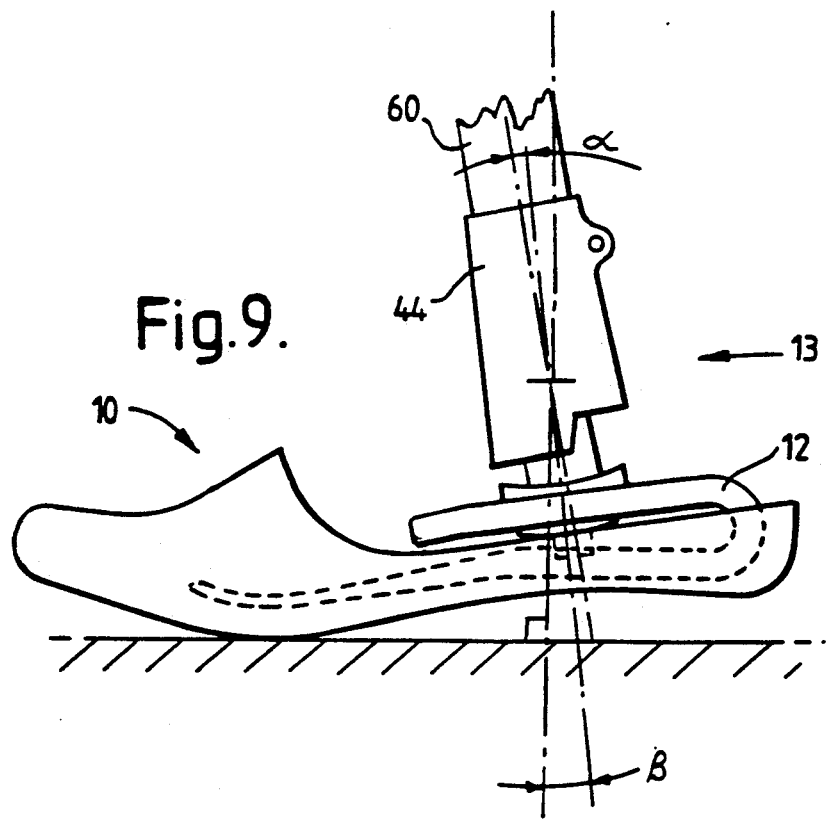
FIG. 9 is an elevation corresponding to that of FIG. 8, showing the prosthesis in a dorsi-flexed condition.

Similarly, referring to FIG. 9, the dorsi-flexion characteristics can be measured by applying a downward force along the shin axis and a dorsi moment about the ankle centre to the shin tube 60.

In this case, the shin tube 60 executes an anti-clockwise movement as seen in FIG. 9, the ankle joint 13 and the keel 12 again contributing to the flexion by angles $\alpha$ and $\beta$ respectively. However, in this case, due to the relative stiffness of the ankle joint 13 in dorsi-flexion, $\alpha$ is less than or equal to $0.3(\alpha+\beta)$. The required downward force and dorsi moment may be produced for test purposes by, again, holding the foot 10 in a nest or cradle so that the heel and ball of the foot remain substantially fixed in position relative to the ground plane, and applying a vertically downwardly directed load on a bracket (not shown) rigidly attached to the shin tube 60, the length and position of the bracket being such that the load acts through a point 100 mm to the anterior of the shin tube 60 and 150 mm above the ankle joint centre of rotation.

What is claimed is:

1. A lower limb prosthesis comprising:
    an energy-storing foot comprising a keel which has an anterior portion and an ankle mounting portion, and is resiliently deformable such that the anterior portion is able to execute an energy-storing dorsi movement relative to the ankle mounting portion, the anterior portion forming part of a lower keel portion extending lengthwise in the foot from a heel part of the foot to an anterior part of the foot, the keel further comprising a posterior connecting portion connecting the ankle mounting portion of the keel to the lower keel portion in the heel part of the foot; and
    an ankle joint assembly having a first part for connection to an upper component of the prosthesis, a second part connected to the ankle mounting portion of the keel, and means connecting the second part to the first part and arranged to allow plantar flexion of the ankle joint assembly from a neutral state but to substantially to prevent dorsi-flexion;
    the foot further comprising a dorsi-flexion restricting device for location between an anterior end part of the ankle mounting portion of the keel and the lower keel portion.

2. A prosthesis according to claim 1, wherein the ankle joint assembly comprises a ball and socket joint having a ball member comprising a ball portion and a connection shank, and a socket member surrounding the ball portion and having an extension in registry with but spaced radially from the shank, wherein the connecting means of the ankle joint assembly comprises buffer means located between the extension and the shank, the buffer being substantially incompressible in respect of dorsi-flexion.

3. A prosthesis according to claim 1, wherein the dorsi-flexion restricting device comprises a buffer element located between the ankle mounting portion of the keel and the lower keel portion at a position to the anterior of an ankle joint centre of the ankle joint assembly.

4. A prosthesis according to claim 3, wherein the buffer element is displaceable from its position between the ankle mounting portion of the keel and the lower keel portion.

5. A prosthesis according to claim 3, wherein the buffer element is a block of elastomeric material.

6. A prosthesis according to claim 5, wherein the buffer element is insertable and removable into and from its location between the said anterior end part and the lower keel portion transversely of the foot.

7. A prosthesis according to claim 4, further comprising an adjustable support member coupling the ankle mounting portion of the keel and lower keel portion ahead of the posterior connecting portion but behind an ankle joint centre of the ankle joint assembly thereby to provide a connection between the ankle mounting portion and the lower keel portion at a position which is variable longitudinally of the foot.

8. An energy-storing artificial foot comprising:
    a keel having an upper load receiving portion, an elongate resiliently deflectable lower portion extending lengthwise in the foot from a heel portion of the foot to an anterior portion of the foot, the load receiving portion being connected to the lower heel portion in the heel portion of the foot;
    a dorsi-flexion restricting device for location between an anterior end part of the load receiving portion and the lower keel portion,
    the load receiving portion including means for securing the foot to an upper limb component;
    the restricting device being located at a position to the anterior of the securing means;
    said restricting device comprising a buffer element comprising a block of elastomeric material, and
    wherein said buffer element is insertable and removable into and from its location between the said anterior end part and the lower keel portion transversely of the foot.

9. An energy-storing artificial foot comprising:
    a keel having an upper load receiving portion, an elongate resiliently deflectable lower portion extending lengthwise in the foot from a heel portion of the foot to an anterior portion of the foot, the load receiving portion being connected to the lower keel portion in the heel portion of the foot;
    a dorsi-flexion restricting device for location between an anterior end part of the load receiving portion and the lower keel portion,
    the load receiving portion including means for securing the foot to an upper limb component;
    the restricting device being located at a position to the anterior of the securing means;
    said restricting device comprising a buffer element;
    said buffer element being displaceable from its position between the load receiving portion and the lower keel portion; and
    an adjustable support member coupling the upper load receiving portion and the lower keel portion, the longitudinal position of the support member being continuously variable.

* * * * *